United States Patent [19]

Rupprecht et al.

[11] Patent Number: 5,695,757
[45] Date of Patent: Dec. 9, 1997

[54] METHODS FOR TREATING POST-EXPOSURE RABIES AND ANTI-RABIES COMPOSITIONS

[75] Inventors: Charles Rupprecht, Sewell, N.J.; Bernhard Dietzschold, Newtown Square; Hilary Koprowski, Wynnewood, both of Pa.

[73] Assignee: Thomas Jefferson University, Philadelphia, Pa.

[21] Appl. No.: 255,557

[22] Filed: Jun. 8, 1994

Related U.S. Application Data

[63] Continuation of Ser. No. 67,718, May 26, 1993, abandoned.
[51] Int. Cl.$^6$ .................. A61K 39/395; C07K 16/08; C07K 16/46
[52] U.S. Cl. .................. 424/133.1; 424/147.1; 424/196.11; 424/178.1; 435/235.1; 530/388.3; 530/387.3
[58] Field of Search .................. 424/133.1, 147.1, 424/196.11, 178.1; 530/387.3, 388.5; 435/235.1

[56] References Cited

FOREIGN PATENT DOCUMENTS 2 188 638   10/1987   United Kingdom .

OTHER PUBLICATIONS

Morrison, Hosp. Pract., 1989, 24:65–69, The Merck Manual of Diagnosis & Therapy, 16th Ed., 1992, pp. 205–208.
Harris and Emery, "Therapeutic Antibodies—the coming of age", TIB TECH 11: 42–44 (1993).

Osband and Ross, "Problems in the investigational study and clinical use of cancer immunotherapy", Immunology Today 11: 193–195 (1990).

Queen et al., "A Humanized Antibody that binds to the Interleukin 2 Receptor", Proc. Natl. Acad. Sci. USA 86: 10029–10033 (1989).

Reichmann et al., "Reshaping Human Antibodies for Therapy", Nature 332: 323–327 (1988).

Schumacher et al., "Use of Mouse Anti-Rabies Monoclonal Antibodies in Postexposure Treatment of Rabies", J. Clin Invest. 84: 971–975 (1989).

Winter and Milstein, "Man-made Antibodies", Nature 349: 293–299 (1991).

Wu and Kabat, "An Analysis of the Sequences of the Variable Regions of Bence Jones Proteins and Myeloma Light Chains and Their Implications for Antibody complementarity", J. Exp. Med 137: 211–250 (1970).

*Primary Examiner*—Frank C. Eisenschenk
*Attorney, Agent, or Firm*—Woodcock Washburn Kurtz Mackiewicz & Norris

[57] ABSTRACT

Pharmaceutical compositions that comprise a pharmaceutically acceptable carrier or diluent and a antibodies that each comprise at least a portion of the variable region from MAb 1112-1 are disclosed. Methods of treating individuals suspected of exposure to rabies are disclosed.

12 Claims, No Drawings

METHODS FOR TREATING POST-EXPOSURE RABIES AND ANTI-RABIES COMPOSITIONS

This is a continuation of application Ser. No. 08/067,718, filed May 26, 1993, now abandoned.

FIELD OF THE INVENTION

The invention relates to a method of treating an individual suspected of having been exposed to rabies virus. More particularly, the present invention relates to administration of a single species of antibodies that is capable of protecting an individual infected with the rabies virus from developing rabies.

BACKGROUND OF THE INVENTION

Rabies, an acute encephalitis (encephalomyelitis), is the result of infection by a group of related lyssaviruses, also referred to herein as rabies viruses. Rabies pathology has been characterized and rabies viruses have been studied; see for example, *The Natural History of Rabies*, 2nd Ed., Edited by G. M. Baer, (1991) CRC Press, which is incorporated herein by reference. Chapter 3 of that reference, Rupprecht, C. E. et al., "Antigenic Relationships of Lyssaviruses", *The Natural History of Rabies*, 2nd Ed., Edited by G. M. Baer, (1991) CRC Press, discloses the antigenic diversity of rabies viruses.

Despite its antiquity, rabies, remains a significant global disease which inevitably results in death. For example, in India, in excess of 500,000 humans annually undergo anti-rabies treatment and more than 50,000 other succumb, primarily due to dog bite. Considering the degree of surveillance and veterinary rabies control efforts in North America, actual human rabies deaths are infrequent. Nevertheless, this vigilance to minimize human mortality supports a huge public health infrastructure and requires the annual treatment of tens of thousands of potential exposure cases; in New York state alone, where there is currently a raccoon rabies epizootic, more than 1,000 people will be treated during 1992 to prevent the disease.

Following the bite of an infected mammal, post-exposure treatment of rabies in humans, as recommended by the World Health Organization, includes proper wound care and the simultaneous administration of multiple doses of an efficacious rabies vaccine, together with anti-rabies immunoglobulin (RIG). However, this treatment regimen presents certain obstacles. Modern inactivated cell culture vaccines and human RIG are a major improvement over historical biologicals prepared from animal origin, but such products are relatively expensive, especially in the developing world where they are most needed, and often in scarce supply.

Schumacher et al., (1989) *J. Clin Invest.* 84:971–975, report studies on antibodies produced by five hybridomas that secrete rabies virus antigen-specific MAbs against G protein (3) and N protein (2). In vitro and in vivo neutralization and protection studies performed using the MAbs singly or as a mixture. The anti-G protein MAbs were shown to effectively neutralize in vitro fixed and street lyssaviruses isolates while the anti-N MAbs did not. In post-exposure experiments in which animals were exposed to the rabies virus and subsequently administered a mixture of the five different species of MAbs, the mixture was demonstrated to be effective to protect animals from lethal rabies virus infection, even in some cases when the mixture was administered 36 hours post exposure. The pre-exposure administration of various single species of anti-G protein MAbs and the mixture of MAbs protected animals when subsequently challenged with a lethal dose of rabies virus while the pre-exposure treatment using anti-N antibodies did not. It was observed that the in vivo protective activity of the anti-G MAb 1112-1 was highest despite that MAb having the lowest in vitro neutralizing activity of the three anti-G MAbs. Schumacher et al. suggest the use of the mixture of different MAbs as a substitute for RIGs used in conventional post-exposure treatment. Schumacher et al. suggest that the risk of side effects in treated individuals brought on by administration of murine MAbs is acceptably low.

There remains a need for potent, inexpensive post-exposure treatments for humans which are useful against a variety of virus strains. There remains a need for a viable substitute for the RIGs currently used. There is a need for treatments which minimize risks of side effects. There is a need for effective compositions useful in post-exposure rabies treatments which are inexpensive and easy to produce in large volumes.

SUMMARY OF THE INVENTION

The present invention relates to pharmaceutical compositions that comprise a single species of antibodies which comprise at least a portion of the variable region from MAb 1112-1 and a pharmaceutically acceptable carrier or diluent.

The present invention relates to a method of treating an individual suspected of having been exposed to rabies comprising administering an effective amount of a pharmaceutical compositions that comprise a single species of antibodies which comprise at least a portion of the variable region from MAb 1112-1 and a pharmaceutically acceptable carrier or diluent.

DETAILED DESCRIPTION OF THE INVENTION

It has been discovered that when administered as a single anti-rabies agent, the murine monoclonal antibody MAb 1112-1, which specifically binds to the IIc epitope of the G protein of rabies virus, is capable of protecting mammals that have been exposed to the rabies virus from lethal rabies infection. It has been discovered that MAb 1112-1 inhibits intercellular spread of rabies virus at a high level. Further, it has been discovered that MAb 1112-1 inhibits transcription of mRNA from rabies virus in infected cells. It has been discovered that post-exposure administration of MAb 1112-1 is able to clear rabies virus from infected cells of the central nervous system (CNS) of infected animals, thereby preventing death from virus-induced encephalomyelitis.

The ability of a single species of antibodies to protect against infection when administered to an individual after exposure to the virus makes such antibodies particularly useful. Pharmaceutical compositions comprising a single species of antibody may be produced inexpensively with relative ease and provide a simple and effective substitute for RIGs currently in use. The simplicity and invariability of such compositions reduces risks associated with antibody-based compositions and allows for less complicated production and quality control as compared to cocktails or RIGs.

According to the present invention, a pharmaceutical composition which comprises an single species of antibodies and pharmaceutically acceptable carrier or diluent. The antibodies of the present invention comprise the specific antigen binding regions, known as complementarity determining regions (CDRs), of MAb 1112-1. The pharmaceutical compositions of the present invention may be used in a method to treat individuals who are suspected of having been exposed to rabies. For example, individuals, including humans or other mammals who have been bitten by animals that may by carriers of the rabies virus, may be administered the pharmaceutical composition of the present invention alone or in combination with other therapeutics.

Administration of a single species of antibodies that have the CDRs of MAb 1112-1, without administration of other antibodies species, is sufficient to effectively prevent the lethal infection in individuals exposed to rabies. Murine MAbs can induce an immune response in humans to mouse Ig allotypes, which may later interfere with the action of other mouse MAbs later used in other therapies. Recombinant DNA techniques minimize this problem by "humanizing" mouse MAb genes. The productively rearranged IgG genes of the hybridoma can be identified by Southern blot analysis by comparison of the patterns of hybridizable bands obtained from restricted DNA of the hybridoma and its parent myeloma using V region probes for the light and heavy chain genes. Size-fractionated DNA containing the productively rearranged genes can be cloned into lambda phage and identified by screening with V region probes. Subsequently, the variable region of the clones genes can be subcloned into a plasmid containing the human constant region genes. Further humanizing of the mouse-human chimeric Ab genes may be achieved by oligonucleotide site-direct mutagenesis. Oligos containing the sequence coding for human framework regions with flanking mouse sequences can be annealed to the mouse-human Ab plasmids, transfected into *E. coli*, and mutated plasmids identified by hybridization with oligonucleotides. By this approach, mouse framework sequences of the variable region would be converted to human sequences so that only the CDRs will contain mouse sequences. Plasmids containing the humanized IgG genes can be expressed by the transfection of light and heavy chain genes into a mouse non-producing myeloma cell line (Sp 2/0).

Murine monoclonal antibody MAb 1112-1 refers to the monoclonal antibody produced by the hybridoma Anti-rabies hybridoma 1112-1, which has been deposited in American Type Culture Collection (12301 Parklawn Drive, Rockville, Md. 20852) and designated accession number HB 10751.

As used herein, the phrase "single species of antibodies" is meant to refer to antibodies which have at least one CDR substantially identical to a CDR in MAb 1112-1. It is preferred that the single species of antibody used in the compositions of the present invention contain more than one MAb 1112-1 CDR, preferably two, more preferably three, more preferably four, more preferably five and most preferably six CDRs substantially identical to the six CDRs of MAb 1112-1. It is preferred that a single species of antibodies is a plurality of identical antibodies.

As used herein, the term "antibody" is meant to refer to complete, intact antibodies, Fab fragments, and F(ab)₂ fragments. It is preferred that antibodies be complete, intact antibodies. The protein structures of complete, intact antibodies, Fab fragments and F(ab)₂ fragments and the organization of the genetic sequences that encode such molecules are well known and are described, for example, in Harlow, E. and D. Lane (1988) *ANTIBODIES: A Laboratory Manual*, Cold Spring Harbor Laboratory, Cold Spring Harbor, N.Y., and in UK Patent Application GB 2,188,638 A published Oct. 7, 1987, both of which are incorporated herein by reference.

As used herein, the term "chimeric antibody" is meant to refer to antibodies which consist of a constant region from an antibody derived from a first species and a variable region in which either the entire variable region or at least a portion of the variable region is derived from a second species.

As used herein, the term "hybrid variable region" refers to a variable region that comprises portions derived from at least two different species. Generally, a hybrid variable region consists of framework sequences from one species and CDRs from a different species.

As used herein, the term "humanized antibodies" is meant to refer to chimeric antibodies that comprise constant regions from human antibodies and hybrid variable regions in which all or most of the framework sequences are from a human variable region and all or most of the CDRs are from a non-human variable region.

The single species of antibodies which are included in the pharmaceutical compositions of the present invention comprise at least one and preferably all of the CDRs of MAb 1112-1. The single species of antibodies which are included in the pharmaceutical compositions of the present invention may be MAb 1112-1 antibodies. Preferably, the single species of antibodies which are included in the pharmaceutical compositions of the present invention are chimeric antibodies which comprise at least a portion of the variable region from MAb 1112-1, including at least one of and preferably more than one of the CDRs, linked to non-murine constant regions, preferably human constant regions. More preferably, the single species of antibodies which are included in the pharmaceutical compositions of the present invention are chimeric antibodies that comprise non-murine constant regions, preferably a human constant regions linked to hybrid variable regions in which the CDRs from MAb 1112-1 are linked to the framework regions from non-human antibodies, preferably human antibodies. The single species of antibodies which are included in the pharmaceutical compositions of the present invention are most preferably humanized antibodies which comprise the CDRs of MAb 1112-1. A used herein, the phrase "at least a portion of the variable region" is meant to refer to the entire amino acid sequence of a variable region or less then the entire amino acid sequence of a variable region provided the portion includes at least one complementarity determining region of the murine monoclonal antibody MAb 1112-1. The antibodies used in the present invention preferably contain heavy and light chains that each comprise at least a portion of the variable region which includes two or, more preferably three complementarity determining regions of murine monoclonal antibody MAb 1112-1. The antibodies used in the present invention preferably comprise only the portions of the variable regions from both the light chain and the heavy chain which consist of the CDRs of murine monoclonal antibody MAb 1112-1. The remaining portions of the variable regions from both the light and heavy chain, the framework portions of the variable region, are preferably from non-murine antibodies, preferably human antibodies.

Murine monoclonal antibody MAb 1112-1 may be produced and isolated utilizing the Anti-rabies hybridoma 1112-1 by employing standard techniques such as those described, for example, in Harlow et al.

Chimeric antibodies are produced by well known recombinant techniques in which the genetic sequences which encode at least a portion of the variable region of MAb 1112-1 including at least one CDR are isolated from Anti-rabies hybridoma 1112-1 and inserted into the genetic sequences that encode a non-murine antibody such that the genetic sequences that encode portions of the non-murine variable region are deleted and replaced with the inserted sequences that encode portions of the MAb1112-1 variable region. Preferred chimeric antibodies, which include non-murine constant regions, non-murine framework regions and MAb 1112-1 CDRs are similarly produced. The genetic sequences which encode the CDR of MAb 1112-1 are isolated from Anti-rabies hybridoma 1112-1 are inserted into the genetic sequences that encode a non-murine antibody such that the genetic sequences that encode the non-murine CDRs are deleted and replaced with the inserted sequences that encode MAb 1112-1 CDRs. Such techniques are described in UK Patent Application GB 2,188,638 A.

As described therein, when chimeric genetic sequences are constructed, some of the genetic sequences that flank the genetic sequences that encode portions that encode the murine CDRs are inserted into the genetic sequences that encode the framework sequences and result in the deletion of some portions of the non-murine framework sequences and substituted with some murine framework sequences. Generally, this substitution of framework sequences is relatively limited and includes only a few amino acid residues of murine framework sequences flanking the murine CDRs. In the course of constructing such chimeric antibodies, it is similarly possible to insert genetic sequences that encode less than complete CDRs into the genetic sequences that encode less than complete frameworks such that the resulting CDRs contain non-murine CDR sequences at one or both ends of the CDR sequence.

Accordingly, as used herein, the term "substantially complete framework sequences" refers to the complete framework sequences except 1–5 residues which flank CDRs and the term "substantially complete CDRs" refers to the complete CDRs of MAb 1112-1 except 1–5 residues which flank framework sequences. Therefore, antibodies according to the present invention which comprise substantially complete non-murine framework sequences may comprise chimeric variable regions which have up to 5 murine framework sequence residues flanking one or both sides of a murine CDR. Similarly, antibodies according to the present invention which comprise substantially complete murine CDR sequences may comprise chimeric variable regions which have up to 5 non-murine CDR sequence residues at one or both sides of and with a murine CDR.

The pharmaceutical compositions may be formulated by one having ordinary skill in the art with compositions selected depending upon the chosen mode of administration. Suitable pharmaceutical carriers are described in *Remington's Pharmaceutical Sciences*, A. Osol, a standard reference text in this field, which is incorporated herein by reference.

The pharmaceutical compositions of the present invention may be administered to an individual suspected of having been exposed to rabies virus by any means that enables the antibodies to come into contact with the free virus and or with infected cells that will display the G protein. Because proteins are subject to being digested when administered orally, parenteral administration, i.e., intravenous, subcutaneous, intramuscular, would ordinarily be used to optimize absorption. The preferred route of administration is intramuscular.

For parenteral administration, the antibodies can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. The liquid vehicle or lyophilized powder may contain additives that maintain isotonicity (e.g., sodium chloride, mannitol) and chemical stability (e.g., buffers and preservatives). The formulation is sterilized by commonly used techniques.

The pharmaceutical compositions according to the present invention may be administered as a single doses or in multiple doses. The pharmaceutical compositions of the present invention may be administered either as individual therapeutic agents or in combination with other therapeutic agents. The treatments of the present invention may be combined with conventional therapies, which may be administered sequentially or simultaneously. For example, the pharmaceutical composition of the present invention is administered in conjunction with a standard rabies vaccine. Thus, the pharmaceutical composition according to the present invention is particularly useful as a replacement for the RIG composition presently used in the standard rabies post-exposure treatment.

The dosage administered varies depending upon factors such as: pharmacodynamic characteristics; its mode and route of administration; age, health, and weight of the recipient; nature and extent of symptoms; kind of concurrent treatment; and frequency of treatment. An effective dose usually contains 0.4 IU to 4000 IU, preferably 4 IU to 400 IU, more preferably 10 IU to 200 IU, more preferably about 40 IU. Usually, a dosage can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

As used herein, the term "effective amount" is meant to refer to the amount of a single species of antibodies comprising at least a portion of the MAb 1112-1 variable region which is sufficient to prevent lethal rabies virus infection in an individual exposed to rabies. Effective amount can be readily determined by routine experimentation.

EXAMPLES

Example 1

Data have been generated which clearly demonstrate that virus neutralization and clearance from the CNS are complex processes and underline the relative importance of humoral immunity in post-exposure protection, as from the passive administration of MAbs. MAb 1112-1 has been shown to be particularly effective in neutralizing rabies virus infection including inhibiting cell to cell spread of virus, reducing RNA transcription in infected cells and clearance of infection from the CNS. Challenge studies in an animal model demonstrate the protection imparted by MAb 1112-1 administered singularly post exposure to the virus. The following is a summary of data.

Thirteen different G protein-specific MAbs, varying in isotype and viral epitope specificity, were compared for their ability to inhibit rabies virus spread in monolayers of neuroblastoma cell culture. The concentration of MAb needed to inhibit virus spread from cell to cell varied considerably. For example, the $ED_{50}$ of MAb that was necessary in inhibition of rabies virus-infected cells was in excess of 10 IU/ml for four MAbs, all of isotype. The $ED_{50}$ of eight other MAbs was greater than or equal to 2.0 IU/ml. In contrast, the $ED_{50}$ of one MAb, 1112-1, was less than or equal to 0.4 IU/ml, and yet virus spread inhibition was still observed at a concentration of 0.08 IU/ml, demonstrating that an extremely small quantity of antibody was effective in reducing viral spread.

Besides inhibition of viral spread, MAbs can also affect the intracellular milieu of infected substrates. For example, treatment of virus-infected neuroblastoma cells by MAbs were used, rabies virus transcription was markedly inhibited only by G protein-specific MAb, 1112-1. Inhibition was most pronounced 18 h post-infection. Rabies RNA transcription inhibition was still observed even when MAb 1112-1 was added 4 h after virus infection.

As a neurotropic virus, rabies can quickly enter the central nervous system. Conventional wisdom has usually held that for intervention in post-exposure treatment to be effective, it must be considered prior to invasion of the nervous system. However, following intranasal inoculation, rabies virus rapidly invades brain tissues; analysis by reverse transcriptase-polymerase chain reaction revealed the presence of rabies virus-specific RNA in the olfactory bulb and cerebral cortex within six to 12 h post-infection. However, treatment of animals with 5 IU of MAb 1112-1 from 1 to 12 h post-infection resulted in a drastic decrease in mortality. Even when the MAb was administered 24 h later, 80% of the animals survived a challenge in which all controls succumbed. Neither virus nor virus-specific RNA could be detected when survivors were euthanized 30 days later. Assay for VNA in the serum of MAb-treated animals demonstrated considerable titers in animals treated from 4 to 24 hours post-infection, similar to time frames in which virus replication occurs.

Example 2

Humanized antibodies are produced using well known techniques and readily available starting materials as follows.

I. Cloning of murine V region genes.

Productively rearranged murine IgG genes of the anti-rabies antibody-producing hybridoma 1112-1 may be identified by Southern blot analysis and subsequently cloned by standard procedures (see Maniatis et.al., Molecular Cloning: A Laboratory Manual, Ch. 9, 1989) which is incorporated herein by reference. Briefly, genomic DNA is partially digested with restriction endonuclease(s) (RE) and the resulting fragments are separated according to size by electrophoresis. The DNA is transferred to a solid support and hybridized to radiolabeled V region probes. Comparison of the pattern of hybridized bands obtained from RE cut DNA from the hybridoma and from the parent myeloma allows for the identification of successfully rearranged light and heavy chain genes. Size fractionated DNA containing the productively rearranged $V_L$ and $V_H$ genes can be cloned into the appropriate lambda phage vector. Briefly, the vector is prepared by cleavage with the appropriate RE(s). The partially digested vector is then ligated with fragments of the murine DNA containing the $V_L$ and $V_H$ genes cut with the same RE(s). The ligated DNA is then packaged into bacteriophage particles according to standard procedures and form plaques on appropriate bacterial hosts. The recombinant bacteriophages are identified by screening with V region probes. After specific clones have been identified by hybridization, they will be characterized by RE digestion and sequenced. Identification of the complimentary determining regions (CDR) and framework (FR) regions can be accomplished by the method described in Wu, T. T. and E. A. Kabat (1970) *J. Exp. Med.* 132:211–250 and Kabat, E. A. et al. (1987) *Sequences of Proteins of Immunologic Interest*, 4th Ed., U.S. Dept. of Health and Human Services, both of which are incorporated herein by reference.

II. Construction of chimeric genes

Genes encoding the chimeric light and heavy chains are separately assembled in appropriate phagemid vectors containing an enhancer, promoter, and polyadenylation signal.

Briefly, gene segments encoding the murine 1112-1 $V_L$ and an appropriate human kappa light chain $C_L$ are joined as are the genes for 1112-1 $V_H$ and an appropriate human IgG C region by subcloning into an acceptable phagemid vector according to standard techniques (see Boyle, A. (1990) *Current Protocols in Molecular Biology*, eds. Ausubel, F. A., et al., Wiley-Interscience/Greene, New York, Ch. 3, pp. 3.0.1–3.18.7, which is incorporated herein by reference).

III. "Humanization" of chimeric genes

Further humanizing of the mouse-human chimeric antibody genes may be achieved by oligonucleotide site-directed mutagenesis. Briefly, sets of oligonucleotides are designed to humanize $V_H$ and $V_L$ murine genes. These oligonucleotides contain regions of the human FR regions as desired. The sets of $V_H$ and $V_L$ humanization oligonucleotides are annealed separately to chimeric $V_H$ and $V_L$ chimeric templates, ligated, and heteroduplex DNA is constructed by extending the oligonucleotide primers with T7 DNA polymerase. The constructs are then transformed into an appropriate strain of *E. coli* where they can be identified by selection and hybridization strategies and can be confirmed for desired sequence by dideoxy chain-termination sequencing.

IV. Expression of humanized genes

Vectors containing the humanized IgG genes from the anti-rabies hybridoma can be expressed by transforming the light and heavy chain constructs into a murine myeloma, which is a non antibody-producing cell line such as Sp2/0 and culturing under conditions of maximum expression. The resulting humanized anti-rabies antibodies can then be analyzed for binding characteristics and protection.

We claim:

1. A method of treating an individual infected with rabies virus and clearing said rabies virus from infected cells of said individual's central nervous system comprising administering a therapeutically effective amount of a pharmaceutical composition comprising:
   a) a single species of antibodies; and
   b) a pharmaceutically acceptable carrier or diluent;
   wherein:
      a) said antibodies each consist of
         i) constant regions from a human antibody, and
         ii) a complete variable region wherein all CDRs are complete CDRs of MAb 1112-1 and framework regions are framework sequences of a human antibody and
      b) said antibodies are capable of neutralizing rabies virus infection in an individual exposed to and infected by rabies virus and clearing rabies virus from infected cells of said individual's central nervous system when said antibodies are administered to said individual after said individual is exposed to and infected by said virus.

2. A method of treating an animal infected with rabies virus and clearing said rabies virus from infected cells of said animal's central nervous system comprising administering a therapeutically effective amount of a pharmaceutical composition comprising
   a) a therapeutically effective amount of a single species of antibodies; and
   b) a pharmaceutically acceptable carrier or diluent;
   wherein:
      a) said antibodies consist of constant regions from non-murine antibodies and variable regions from MAb 1112-1; and
      b) said antibodies are capable of neutralizing rabies virus infection in an animal infected by rabies virus and clearing rabies virus from infected cells of said animal's central nervous system when said antibodies are administered to said animal after said animal is exposed to and infected by said virus.

3. The method of claim 2 wherein said constant regions are human constant regions.

4. The method of claim 1 wherein:
   a) constant regions of said antibodies are human constant regions;
   b) framework sequences of said antibodies are complete framework sequences of a human antibody; and
   c) all CDRs of said antibodies are complete CDRs of MAb 1112-1.

5. The method of claim 1 further comprising the step of administering a rabies vaccine.

6. A method of treating an animal infected with rabies comprising administering a therapeutically effective amount of a pharmaceutical composition comprising:
   a) a single species of antibodies; and
   b) a pharmaceutically acceptable carrier or diluent;
wherein said antibodies are MAb 1112-1.

7. The method of claim 6 further comprising the step of administering a rabies vaccine.

8. A pharmaceutical composition for the treatment of an individual infected with rabies comprising:
   a) a therapeutically effective amount of a single species of antibodies; and
   b) a pharmaceutically acceptable carrier or diluent;
   wherein:
      a) said antibodies each consist of
         i) constant regions from a human antibody, and
         ii) a complete variable region wherein all CDRs are complete CDRs of MAb 1112-1 and framework regions are framework sequences of a human antibody and
      b) said antibodies are capable of neutralizing rabies virus infection in an animal exposed to and infected by rabies virus and clearing rabies virus from infected cells of said animal's central nervous system when said antibodies are administered to said animal after said animal is exposed to and infected by said virus.

9. A pharmaceutical composition for the treatment of an individual infected with rabies comprising:
   a) a therapeutically effective amount of a single species of antibodies; and
   b) a pharmaceutically acceptable carrier or diluent;
   wherein:
      a) said antibodies consist of constant regions from non-murine antibodies and variable regions from MAb 1112-1; and
      b) said antibodies are capable of neutralizing rabies virus infection in an animal exposed to and infected by rabies virus and clearing rabies virus from infected cells of said animal's central nervous system when said antibodies are administered to said animal after said animal is exposed to and infected by said virus.

10. The pharmaceutical composition of claim 9 wherein said constant regions are human constant regions.

11. The pharmaceutical composition of claim 1 wherein:
    a) constant regions of said antibodies are human constant regions;
    b) framework sequences of said antibodies are complete framework sequences of a human antibody; and
    c) all CDRs of said antibodies are complete CDRs of MAb 1112-1.

12. The pharmaceutical composition of claim 1 further comprising a rabies vaccine.

* * * * *